Figure 1:
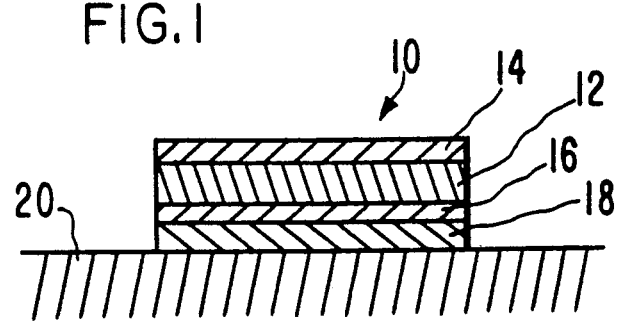

United States Patent [19]
Ledger et al.

[11] Patent Number: 5,149,539
[45] Date of Patent: *Sep. 22, 1992

[54] REDUCTION OR PREVENTION OF SENSITIZATION TO DRUGS

[75] Inventors: Philip W. Ledger; Michel J. N. Cormier, both of Mountain View; Alfred Amkraut, Palo Alto, all of Calif.

[73] Assignee: ALZA Corporation, Palo Alto, Calif.

[*] Notice: The portion of the term of this patent subsequent to Jul. 14, 2009 has been disclaimed.

[21] Appl. No.: 793,936
[22] Filed: Nov. 15, 1991

Related U.S. Application Data

[63] Continuation of Ser. No. 562,788, Aug. 3, 1990, Pat. No. 5,120,545.

[51] Int. Cl.$^5$ .............................. A61F 13/00
[52] U.S. Cl. ................... 424/449; 424/448
[58] Field of Search ................. 424/448, 449

[56] References Cited

U.S. PATENT DOCUMENTS

| | | | |
|---|---|---|---|
| 3,598,122 | 11/1971 | Zaffaroni | 128/268 |
| 3,598,123 | 8/1971 | Zaffaroni | 128/268 |
| 3,991,755 | 11/1976 | Vernon et al. | 128/172.1 |
| 4,141,359 | 2/1979 | Jacobsen et al. | 128/172.1 |
| 4,250,878 | 2/1981 | Jacobsen et al. | 128/207.21 |
| 4,274,420 | 6/1981 | Hymes | 128/641 |
| 4,286,592 | 9/1981 | Chandrasekaran | 128/260 |
| 4,314,557 | 2/1982 | Chandrasekaran | 128/260 |
| 4,325,367 | 4/1982 | Tapper | 128/207.21 |
| 4,379,454 | 4/1983 | Campbell et al. | 604/897 |
| 4,391,278 | 7/1983 | Cahalan et al. | 128/640 |
| 4,398,545 | 8/1983 | Wilson | 128/798 |
| 4,419,092 | 12/1983 | Jacobsen et al. | 604/20 |
| 4,474,570 | 10/1984 | Ariura et al. | 604/20 |
| 4,557,723 | 12/1985 | Sibalis | 604/20 |
| 4,559,222 | 12/1985 | Enscore et al. | 424/28 |
| 4,573,995 | 3/1986 | Chen et al. | 604/896 |
| 4,640,689 | 2/1987 | Sibalis | 604/20 |
| 4,702,732 | 10/1987 | Powers et al. | 604/20 |
| 4,708,716 | 11/1987 | Sibalis | 604/20 |
| 4,885,154 | 12/1989 | Cormier et al. | 424/10 |

OTHER PUBLICATIONS

Friedmann, Current Opinion Immunology 1:690-693 (1989).

Aiba et al., Clinical Research 38:283A (1990).
Ziegler et al., Proc. Natl. Acad. Sci. USA 79:175-178 (1982).
Jensen, J. Exp. Med. 171:1779-1784 (1990).
Tietze et al., Biochem. Biophys. Res. Commun. 93:1-8 (1980).
Mellman et al., Ann. Rev. Biochem. 55:663-700 (1986).
Joshi et al., Cellular Immunology 125:518-525 (1990).
Maxfield, J. Cell Biol. 95:676-681 (1982).
Ohkuma et al., Proc. Natl. Acad. Sci. USA 75:3327-3331 (1978).
Pressman, Chapter 6, in, Eichhorn (ed.) "Inorganic Biochemistry", vol. 1, pp. 203-226, Elsevier Scientific Publishing Co., New York, 1973.
Vestal et al., J. Parmacol. Exp. Therap. 214:106-111 (1980).

Primary Examiner—Thurman K. Page
Assistant Examiner—D. Gabrielle Phelan
Attorney, Agent, or Firm—Jacqueline S. Larson; Edward L. Mandell; Steven F. Stone

[57] ABSTRACT

The present invention is directed to a method of reducing or preventing skin sensitization by inhibiting the immunological processing of a sensitizing drug as an antigen. The drug is sensitizing to humans, i.e., the drug is susceptible to inducing skin or mucosa sensitization in a human when the drug is transdermally administered to the human at a therapeutically effective rate. Skin sensitization reduction or prevention is induced by coadministering to the skin or mucosa of the human:
(a) a therapeutically effective amount of a sensitizing drug, at a therapeutically effective rate over a predetermined period of time; and
(b) an antigen processing-inhibiting agent in an amount effective to inhibit the antigen processing of the drug.

The system of the invention comprises a matrix adapted to be placed in sensitizing drug and antigen processing-inhibiting agent transmitting relation to the selected skin or mucosa site. The matrix contains sufficient amounts of the drug and the agent to continuously coadminister to the skin or mucosa site the drug, at a therapeutically effective rate and over a predetermined delivery period, and the antigen processing-inhibiting agent, at a rate and for a period of time sufficient to inhibit the processing of the drug as an antigen.

16 Claims, 2 Drawing Sheets

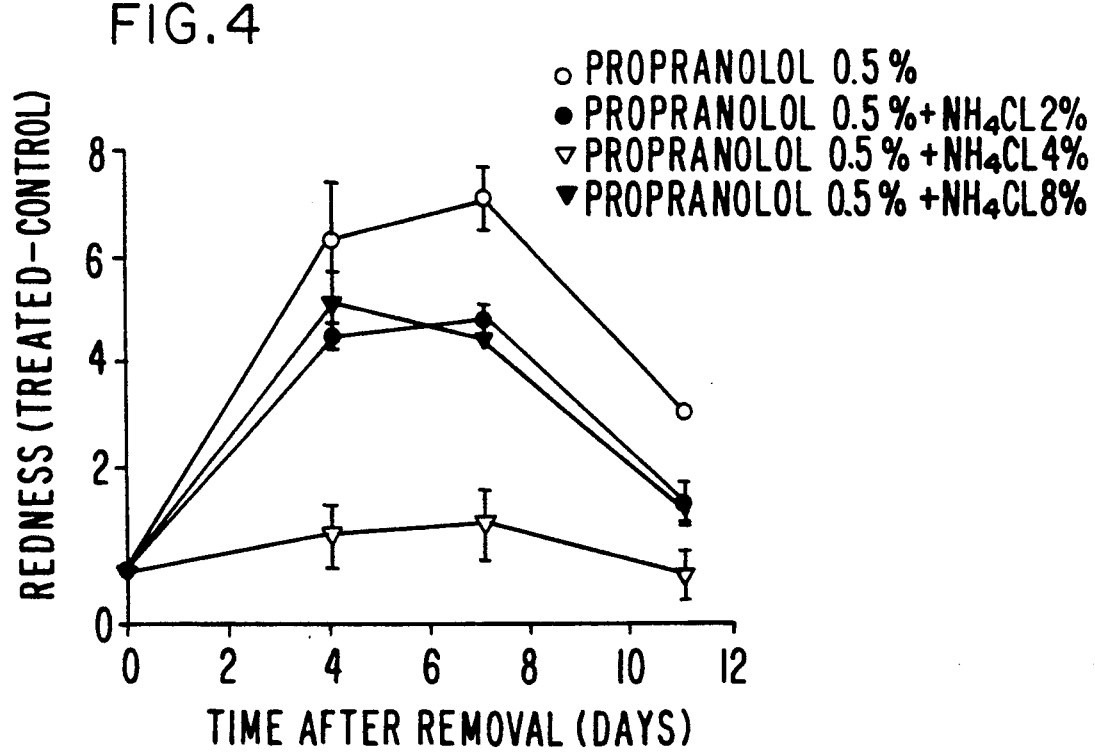

REDUCTION OR PREVENTION OF SENSITIZATION TO DRUGS

This application is a continuation of application Ser. No. 07/562,788, filed Aug. 3, 1990, now U.S. Pat. No. 5,120,545 and benefit of the filing date of said earlier filed application is claimed under 35 U.S.C. §120.

CROSS-REFERENCE TO RELATED APPLICATIONS

This invention is related to the inventions disclosed in the copending, coassigned patent applications Ser. No. 07/217,014 filed on Jul. 8, 1988, U.S. Pat. No. 4,000,956 of Amkraut et al., for Prevention of Contact Allergy by Coadministration of a Corticosteroid with a Sensitizing Drug; Ser. No. 07/364,932 filed on Jun. 9, 1989, U.S. Pat. No. 5,049,387 of Amkraut, for Inducing Skin Tolerance to a Sensitizing Drug; and Ser. No. 07/549,584 filed on Jul. 6, 1990, of Cormier et al., for Reduction or Prevention of Skin Irritation by Drugs.

FIELD OF THE INVENTION

This invention relates to the transdermal delivery of drugs. More particularly, this invention relates to the reduction or elimination of sensitization responses caused by the immunological processing of certain sensitizing drugs in intracellular vesicles such as the lysosomes.

DESCRIPTION OF TERMS

As used herein, the term "drug" refers to a biologically active agent, compound or composition of matter which is administered for the purpose of providing some beneficial or therapeutic effect.

As used herein, the term "transdermal" delivery or application refers to the delivery or application of agents by passage through skin, mucosa and/or other body surfaces by topical application or by iontophoresis.

As used herein, the term "therapeutically effective" amount or rate refers to the amount or rate of drug or agent needed to effect the desired beneficial or therapeutic result.

BACKGROUND OF THE INVENTION

The transdermal route of parenteral drug delivery provides many advantages. Unfortunately, however, many drugs which appear to be ideal candidates for transdermal delivery have a tendency to cause undesirable skin reactions, conditions known as contact sensitivity or contact allergy. Therefore, despite the development of the transdermal drug delivery art, there remains a continuing need for an improved method of overcoming contact sensitization caused by transdermal delivery of a sensitizing drug.

Sensitization is a two-phase process involving distinct biological mechanisms of the human immune system. The first phase is called the induction phase. Induction occurs when the skin of an individual is first exposed to the sensitizing drug. In this phase, the sensitizing drug or antigen is presented to the T lymphocytes (T cells) by the Langerhans cells of the epidermis, either in situ or in the draining lymph node. As a consequence, T cells which recognize the antigen proliferate and to some extent differentiate. Generally, no visible skin reaction is noted during the induction phase. Following induction, some of the individual's lymphocytes are specifically sensitized to the drug.

The second phase of sensitization is called elicitation. Elicitation occurs when the individual is subsequently (i.e., after induction) exposed to the same sensitizing drug. Elicitation causes a skin reaction to occur. The skin reaction occurring during elicitation is known as contact dermatitis. During elicitation, the antigen is once again presented mainly on the Langerhans cells. The T cells, which have proliferated upon prior exposure to the drug (i.e., during the induction phase), now come to the treated site and initiate events which result in local inflammation or contact dermatitis.

Irritation, on the other hand, is a completely different phenomenon from contact (i.e., skin) sensitization. Skin irritation can be caused by a variety of factors including, but not limited to, physical factors (e.g., chafing or occluding the skin in an airtight manner), exposure to certain chemicals, exposure to pH outside the normal pH range of the skin or mucosa, and bacterial overgrowth. Generally, tissue irritation is the manifested result of damage or toxicity to cells in the skin or mucosa caused by their response to a cytotoxic (i.e., irritating) agent. Sensitization, on the other hand, is the result of a response by the immune system to an agent (i.e., an antigen) which is not necessarily irritating.

In general, once the skin has become sensitized, skin reactions occurring after re-exposure to the sensitizing agent are difficult to prevent. For this reason, this invention is directed towards preventing sensitization from occurring, as well as reducing or eliminating pain and discomfort occurring during the elicitation phase after sensitization has already been induced.

It is generally accepted that recognition of an antigen by a T cell during either the induction or the elicitation phase requires that the antigen be associated with a particular molecule (a "class II MHC molecule") on the surface of an antigen presenting cell (APC). This process is termed "antigen presentation". Typical APCs are macrophages and, in the epidermis, Langerhans cells (Friedmann, Curr. Opin. Immunol., 1989, 1:690-693; Aiba et al., Clin. Res., 1990, 38:283A). For presentation to occur, the antigen must be converted to an appropriate form for association with the MHC. Events that lead to the association of an antigen with the cell surface of a class II MHC molecule are collectively referred to as "antigen processing". Processing involves the uptake by an APC of an antigen into acidic intracellular vesicles such as the lysosomes where it is exposed to proteases so that the antigen, if it is a large proteintype molecule, is physically or chemically altered (Ziegler et al., Proc. Natl. Acad. Sci. USA, 1982, 79:175-178). Class II MHC molecules then associate with the antigenic moiety, intracellularly, whereupon the complex is transported to the surface membrane of the APC. Only then will the antigen be effectively recognized by the T cells.

The low pH of intracellular vesicles has been shown to be a factor in regulating the formation of functional antigen/class II MHC complexes. Ziegler et al. (ibid.) have found that by using lysosomotropic agents such as chloroquine or ammonia to increase the lysosomal pH, the activity of the proteases in the lysosomes is decreased, which proteases appear to interact with at least certain antigenic moieties during processing. It has also been found that the binding of antigen to class II MHC molecules is slow at neutral pH but is accelerated and enhanced in an acidic environment (Jensen, J. Exp.

Med., 1990, 171:1779-1784). In addition, low lysosomal pH is a factor in regulating the recycling of receptor molecules in the vesicles, so that when the pH is raised, the rate of recycling is reduced (Tietze et al., Biochen. Biophys. Res. Commun., 1980, 93:1-8; Mellman et al., Ann. Rev. Biochem., 1986, 55:663-700; Joshi et al., Cell Immunol., 1990, 125:518-525). This reduction of recycling could reduce the contact between class II MHC molecules and antigen, resulting in fewer complexes being formed.

Lysosomes are small membrane-enclosed organelles which are found within almost all animal cells. Under normal conditions, lysosomes have an internal pH in the range of 4.5 to 5. In contrast, the physiological pH outside the cell is about 7.0. This difference can result in extensive accumulation within the lysosomes of weak bases. The weak bases can permeate the cell and the lysosomal membranes in their uncharged molecular form. However, the low internal pH of lysosomes favors protonation of the weak base molecules; once they are charged, the molecules are relatively membrane-impermeable and less able to pass back through the membrane. Such accumulation of weak bases will raise the pH in the lysosome (Maxfield, J. Cell Biol., 1982, 95:676-681; Ohkuma et al., Proc. Natl. Acad. Sci. USA, 1978, 75:3327-3331).

Other compounds, the ionophores, have also been shown to raise the pH in lysosomes (Maxfield, ibid.; Ohkuma et al., ibid.). The ionophores incorporate in the lysosomal membranes and facilitate the exchange of ions, thereby destroying the normally-existing pH gradient (Pressman, "Alkali Metal Chelators - The Ionophores", in, Eichhorn, ed., Inorganic Biochemistry, Vol. 1, pp. 218-221, Elsevier Scientific Publishing Co., N.Y., 1973).

SUMMARY OF THE INVENTION

It is an object of the present invention to reduce or prevent sensitization in a human patient caused by the transdermal administration to the patient of a sensitizing drug.

This and other objects, features and advantages are met by the present invention which provides a method of reducing or preventing skin sensitization by inhibiting the immunological processing of a sensitizing drug as an antigen. The drug is sensitizing to humans, i.e., the drug is susceptible to inducing skin or mucosa sensitization in a human when the drug is transdermally administered to the human at a therapeutically effective rate. Skin sensitization reduction or prevention is induced by coadministering to the skin or mucosa of the human:

(a) a therapeutically effective amount of a sensitizing drug, at a therapeutically effective rate over a predetermined period of time; and (b) an antigen processing-inhibiting agent in an amount effective to inhibit the processing of the drug as an antigen.

The system of the invention comprises a matrix adapted to be placed in sensitizing drug and antigen processing-inhibiting agent transmitting relation to the selected skin or mucosa site. The matrix contains sufficient amounts of the drug and the agent to continuously coadminister to the skin or mucosa site the drug, at a therapeutically effective rate and over a predetermined delivery period, and the antigen processing-inhibiting agent, at a rate and for a period of time sufficient to inhibit the processing of the drug as an antigen. A device for carrying out the invention may be either a passive transdermal device or an active transdermal device where transport of the agent is assisted by electric, sonic, thermal or other energy source.

BRIEF DESCRIPTION OF THE DRAWINGS

FIG. 1 is a cross-sectional view of one embodiment of a transdermal therapeutic device which may be used in accordance with the present invention.

FIG. 2 is a cross-sectional view of another embodiment of a transdermal therapeutic device which may be used in accordance with the present invention.

FIG. 3 is a schematic view of an iontophoretic drug delivery device which may be used in accordance with the present invention.

FIG. 4 illustrates graphically the reduction in elicitation of sensitization to propranolol by coadministration of propranolol with ammonium chloride.

DETAILED DESCRIPTION OF THE INVENTION

According to the present invention, transdermal coadministration of a sensitizing drug with an antigen processing-inhibiting agent reduces or prevents sensitization in humans by inhibiting the processing of the sensitizing drug as an antigen. This inhibition can take place at either the induction phase or the elicitation phase of antigenic skin sensitization.

The present invention is applicable to any chemical agent or drug which is normally delivered through body surfaces and membranes, including skin and mucosa, and which tends to cause contact sensitivity or contact allergy to a human as a result of antigenic sensitization following transdermal application of the compound to the skin or mucosa. These are compounds which are capable of being processed in and presented by the Langerhans or other cells as an antigen, resulting in sensitization of the T lymphocytes. As used herein, the expressions "drug" and "agent" are used interchangeably and are intended to have their broadest interpretation as to any therapeutically active substance which is delivered to a human to produce a desired, usually beneficial, effect. In general, this includes therapeutic agents in all of the major therapeutic areas, including, but not limited to, anti-infectives such as antibiotics and antiviral agents, analgesics and analgesic combinations, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics including gastrointestinal and urinary, anticholinergics, sympatholytics, sympathomimetrics, xanthine derivatives, cardiovascular preparations including calcium channel blockers and beta-blockers, antiarrythmics, antihypertensives, diuretics, vasodilators including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, psychostimulants, sedatives, tranquilizers, local anesthetics, opiate agonists, opiate antagonists, and pharmacologically active peptides, polypeptides and proteins. Examples of representative drugs within these classes include, by way of example and not for purposes of limitation, ketoprofen, piroxicam, indomethacin, scopolamine, imipramine, desipramine, nortriptyline, clemastine, chlorpheniramine, diphenhydramine, daunorubicin, chloroquine, quinacrine, chlorpromazine, fluphenazine, perphenazine, propranolol, alprenolol, betaxolol, labetalol, metoprolol, timolol, pindolol, atenolol, tetracaine, prilocaine, buprenorphine, naloxone, naltrexone, phentolamine, phenylpropanolamine, ephedrine, mephentermine, bitolterol, tolazoline, streptomycin, gentamycin, somatropin, somatotropin, somatostatin, insulin, insulin-like growth factor (somatomedins), luteinizing hormone releasing hormone, tissue plasminogen activator, and growth hormone releasing hormone.

Since a low pH, acidic intracellular environment appears to be necessary, or at least advantageous, to the processing and presentation of an antigen to cause a contact sensitization response in a human, those compositions that raise the intracellular pH of low pH organelles, and particularly the intralysosomal pH, of the Langerhans cells or other antigen presenting cells of the skin would be effective as antigen processing-inhibiting agents.

The pH within the lysosomes can be raised in at least two different ways. The first is through the action upon lysosomal membranes by an agent that interferes with ion pumps and thereby allows the intralysosomal pH to rise, destroying the pH gradient and lessening the tendency to ionize compounds that may enter. Examples of such interfering agents are the ionophores, such as monensin, (R)(+)-1,1'-bi-2-naphthol, nigericin, valinomycin, gramicidin D, A23187, and carbonyl cyanide m-chlorophenylhydrazone. The second mode of action is the uptake and accumulation of basic molecules and the resulting competition for available charge in the low pH lysosomal micro-environment. These weak bases raise the pH within the lysosomes as they accumulate. Examples of such weak base compounds are amphiphilic cations and include amphiphilic amines, such as ammonia and its salts (ammonium chloride being an example), low molecular weight amines (such as methylamine, diethylamine and isopropylamine) and their salts, and aminoalcohols (such as ethanolamine, diethanolamine, triethanolamine and tromethamine) and their salts. In a presently preferred embodiment, accumulative weak base compounds, and particularly the amphiphilic amines, are preferred as the antigen processing-inhibiting agent.

The antigen processing-inhibiting agents can be selected from those exhibiting one or the other or both of the above two modes of action, or they may be selected from other compounds that work by otherwise raising the intracellular, particularly the intralysosomal, pH or by mechanisms not presently known. The basic requirement of an antigen processing-inhibiting agent under the present invention is that it inhibit the cellular pathway of antigen processing so that it inhibits the processing of a sensitizing drug or a biotransformation product of a drug as an antigen.

In this invention, the antigen processing-inhibiting agent is continuously and co-extensively administered with the sensitizing drug and to the same skin or mucosa as the drug in an amount sufficient to reduce or prevent sensitization by the drug in the human. For any given drug and antigen processing-inhibiting agent combination, the amount can be experimentally determined by those skilled in the art.

In one embodiment of the invention, the antigen processing-inhibiting agent should be coadministered with the drug throughout all or almost all of the time period during which the drug is administered. This is particularly the case when the agent, once removed from the treatment site, quickly loses its inhibiting action; that is, once the agent is removed, the internal pH within the lysosomes will begin to return to its normal lower level and as the pH lowers, the drug will begin to be processed as an antigen, causing sensitization in the patient. This is of particular concern when administration takes place over a relatively long period of time, such as greater than 24 hours. In another embodiment of the invention, continuous coadministration of the drug and an antigen processing-inhibiting agent is not required when the agent continues to exert an action on the lysosomes for an extended period after it is removed from the treatment site. In such cases, the drug and the agent are coadministered to a site for a sufficient period of time to cause inhibition of the antigenic processing of the drug, after which time the drug alone may continue to be administered to the site.

In addition to coadministering the antigen processing-inhibiting agent during administration of the drug, it is desirable in some instances to pretreat the skin or mucosal administration site with the agent prior to application of the drug. This pretreatment will depend on the particular processing-inhibiting agent chosen as well as the drug to be used. In this manner, the lysosomal pH will have been sufficiently altered to inhibit antigen processing before the drug is present. Pretreatment with the agent is especially useful when the agent is slow to affect the lysosomal pH or when the drug has a very rapid rate of entry into or processing within the lysosome.

According to the present invention, one or more antigen processing-inhibiting agents and the sensitizing drug are placed in drug and antigen processing-inhibiting agent transmitting relation with the appropriate body surface, preferably suspended in a carrier therefor, and maintained in place for the desired period of time. The drug and agent are typically dispersed within a physiologically compatible matrix or carrier which may be applied directly to the body as an ointment, gel, cream, suppository or sublingual or buccal tablet, for example, or they may be administered from a matrix or carrier in a transdermal therapeutic delivery device or an iontophoretic delivery device.

The transdermal route of parenteral delivery of drugs provides many advantages, and transdermal therapeutic devices for delivering a wide variety of drugs or other beneficial agents are well known in the art. Typical devices are described in U.S. Pat. Nos. 3,598,122, 3,598,123, 4,286,592, 4,314,557, 4,379,454, 4,559,222 and 4,573,995, for example, all of which are incorporated herein by reference. The coadministration of an antigen processing-inhibiting agent and a sensitizing drug as disclosed herein can be accomplished using transdermal devices of these kinds.

In order to ensure co-extensive administration of drug and antigen processing-inhibiting agent to skin or mucosa, it is preferred to administer the drug and agent from a matrix (e.g., a drug- and agent-containing matrix) in a transdermal delivery device, which matrix is placed in drug and antigen processing-inhibiting agent transmitting relation with the skin or mucosa.

Two examples of suitable transdermal delivery devices are illustrated in FIGS. 1 and 2. In FIG. 1, transdermal delivery device 10 comprises a reservoir 12 containing both a sensitizing drug and an antigen processing-inhibiting agent. Reservoir 12 is preferably in the form of a matrix containing the drug and agent dispersed therein. Reservoir 12 is sandwiched between a backing layer 14, which is impermeable to both the drug and the agent, and a rate-controlling membrane 16. In FIG. 1, the reservoir 12 is formed of a material, such as a rubbery polymer, that is sufficiently viscous to maintain its shape. If a lower viscosity material is used for reservoir 12, such as an aqueous gel, backing layer 14 and rate-controlling membrane 16 would be sealed together about their periphery to prevent leakage. The device 10 adheres to the surface of the skin 20 by means of an in-line contact adhesive layer 18. The adhesive layer 18 may optionally contain agent and/or drug. A strippable release liner (not shown) is normally provided along the exposed surface of adhesive layer 18 and is removed prior to application of device 10 to the skin 20.

Figure 2:
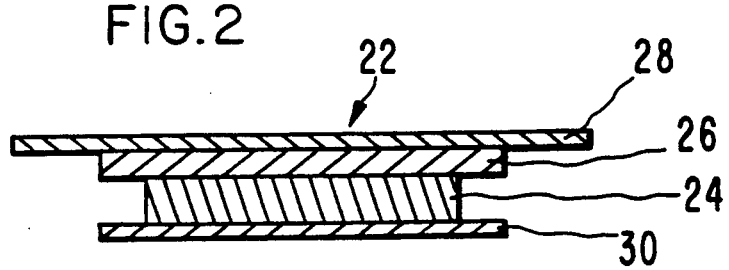

Alternatively, as shown in FIG. 2, transdermal therapeutic device 22 may be attached to the skin or mucosa of a patient by means of an adhesive overlay 28. Device 22 is comprised of a drug- and agent-containing reservoir 24 which is preferably in the form of a matrix containing the drug and the agent dispersed therein. An impermeable backing layer 26 is provided adjacent one surface of reservoir 24. Adhesive overlay 28 maintains the device on the skin and may be fabricated together with, or provided separately from, the remaining elements of the device. With certain formulations, the adhesive overlay 28 may be preferable to the in-line contact adhesive 18 as shown in FIG. 1. This is true, for example, where the drug/agent reservoir contains a material (such as, for example, an oily surfactant permeation enhancer) which adversely affects the adhesive properties of the in-line contact adhesive layer 18. Impermeable backing layer 26 is preferably slightly larger than reservoir 24, and in this manner prevents the materials in reservoir 24 from adversely interacting with the adhesive in overlay 28. Optionally, a rate-controlling membrane (not shown in FIG. 2) similar to membrane 16 in FIG. 1 may be provided on the skin/mucosa side of reservoir 24. A strippable release liner 30 is also provided with device 22 and is removed just prior to application of device 22 to the skin.

In those cases where it is desired to pretreat the skin or mucosa with the antigen processing-inhibiting agent prior to coadministration of drug/agent or where the drug flux is much greater than the agent flux, an amount of the agent may be present in the adhesive layer 18. On the other hand, where it is not necessary to pretreat the application site or where there is no great disparity between drug and agent fluxes, both the drug and the agent may be delivered from the adhesive layer 18 as well as from the reservoir 24.

The drug and the antigen processing-inhibiting agent can be coextensively administered to human skin or mucosa by direct application to the skin or mucosa in the form of an ointment, gel, cream or lotion, for example, but is preferably administered from a skin patch or other known transdermal delivery device which contains a saturated or unsaturated formulation of the drug and the agent. The formulation may be aqueous or non-aqueous based. The formulation should be designed to deliver the sensitizing drug and the antigen processing-inhibiting agent at the necessary fluxes. Depending on the drug to be delivered, the drug and agent carrier(s) may be either aqueous or non-aqueous based. Aqueous formulations typically comprise water and about 1-2 weight % of a hydrophilic polymer as a gelling agent, such as hydroxyethylcellulose or hydroxypropylcellulose. Typical non-aqueous gels are comprised of silicone fluid or mineral oil. Mineral oil-based gels also typically contain 1-2 weight % of a gelling agent such as colloidal silicon dioxide. The suitability of a particular gel depends upon the compatibility of its constituents with both the sensitizing drug and the antigen processing-inhibiting agent, along with a permeation enhancer, if one is present, and any other components in the formulation.

The reservoir matrix should be compatible with the drug, the antigen processing-inhibiting agent and any carrier therefor. When using an aqueous-based system, the reservoir matrix is preferably a hydrophilic polymer, e.g., a hydrogel. When using a non-aqueous-based system, the reservoir matrix is preferably composed of a hydrophobic polymer. Suitable polymeric matrices are well known in the transdermal drug delivery art, and examples are listed in the above-named patents previously incorporated herein by reference.

When a constant drug delivery rate is desired, the sensitizing drug is present in the matrix or carrier at a concentration in excess of saturation, the amount of excess being a function of the desired length of the drug delivery period of the system. The drug may, however, be present at a level below saturation without departing from this invention as long as the drug and the antigen processing-inhibiting agent are continuously and coextensively administered to the same skin or mucosa site in an amount and for a period of time sufficient to reduce or eliminate skin sensitization by the drug.

In addition to the sensitizing drug and the antigen processing-inhibiting agent, which are essentially to the invention, the matrix or carrier may also contain dyes, pigments, inert fillers, permeation enhancers (of either the drug or the inhibiting agent or for both), excipients and other conventional components of pharmaceutical products or transdermal devices known to the art.

Drugs may also be delivered transdermally by iontophoresis, and iontophoretic devices for delivering a wide variety of drugs or other beneficial agents are well known in the art. Iontophoretic delivery devices include a donor electrode assembly which includes a donor electrode and a reservoir containing the beneficial agent to be iontophoretically delivered. The donor electrode assembly is adapted to be placed in agent transmitting a relation with the skin or mucosa of the patient. The device also includes a counter electrode assembly adapted to be placed in electrical contact with the skin at a location spaced apart from the donor electrode. Further, the device includes an electric power source. The electrodes and the power source are electrically connected and form a closed circuit when the electrode assemblies are placed in current conducting relation with the skin of the patient. The coadministration of an antigen processing-inhibiting agent and a sensitizing drug as disclosed herein can be accomplished using any iontophoretic device. Typical devices are described in U.S. Pat. Nos. 3,991,755, 4,141,359, 4,250,878, 4,274,420, 4,325,367, 4,391,278, 4,398,545, 4,419,092, 4,474,540, 4,557,723, 4,640,689, 4,702,732 and 4,708,716, for example, all of which are incorporated herein by reference.

Figure 3:
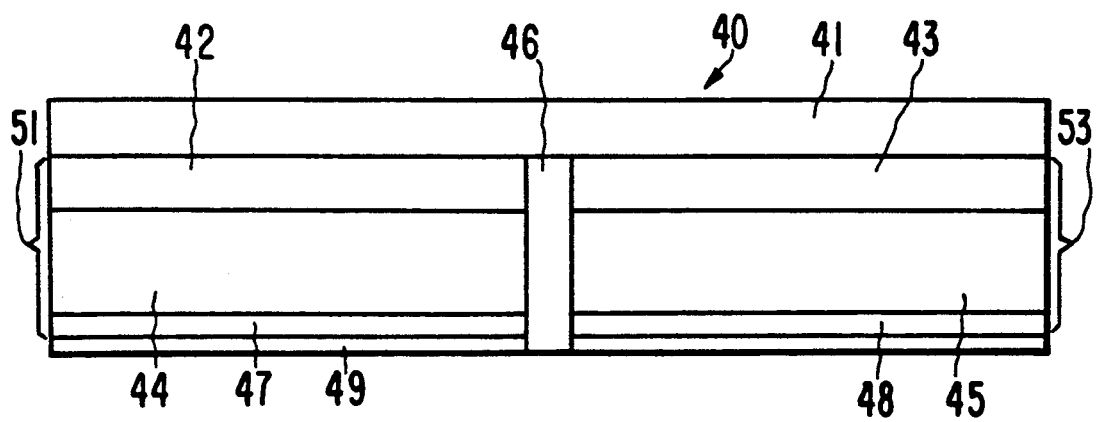

FIG. 3 illustrates one example of a preferred iontophoretic delivery device 40. Device 40 has a top layer 41 which contains an electrical power supply (e.g., a battery or a series of batteries) as well as optional control circuitry such as a current controller (e.g., a resistor or a transistor-based current control circuit), an on/off switch, and/or a microprocessor adapted to control the current output of the power source over time. Device 40 also includes electrode assembly 51 and electrode assembly 53. Electrode assemblies 51 and 53 are separated from one another by an electrical insulator 46 and form therewith a single self-contained unit. For purposes of illustration, the electrode assembly 51 will be referred to as the "donor" electrode assembly while electrode assembly 53 will be referred to as the "counter" electrode assembly. In this embodiment, the donor electrode 42 is positioned adjacent drug reservoir 44 while the counter electrode 43 is positioned adjacent the return reservoir 45 which contains an electrolyte. Electrodes 42 and 43 are formed from metal foils (such as silver or zinc) or a polymer matrix loaded with metal powder, powdered graphite, carbon fibers or any other suitable electrically conductive material. Reservoirs 44 and 45 can be polymeric matrices or gel matrices. Insulator 46 is composed of a non-electrical conducting and non-ion-conducting material which acts as a barrier to prevent short-circuiting polymer or adhesive or other suitable barrier to ion flow. The device 40 is adhered to the skin by means of ion-conducting adhesive layers 47 and 48. The device 40 also includes a strippable release liner 49 which is removed just prior to application to the skin.

In a typical device 40, the drug reservoir 44 contains an ionizable supply of the drug to be delivered together with the antigen processing-inhibiting agent, and the counter reservoir 45 contains a suitable electrolyte. In this way, the positive drug ions are delivered through the skin from the anode electrode assembly. The drug reservoir 44 of the iontophoretic delivery device 40 must be in drug and processing-inhibiting agent relation with the skin or mucosa. It is not necessary, however, that the return reservoir 45 be in electrolyte transmitting relation with the skin or mucosa, although this is preferred. It has been found to be preferable to use a water-soluble salt of the drug or agent to be delivered.

In the present invention, the drug is delivered at a therapeutically effective rate and the agent is delivered at an antigen processing-inhibiting rate for a predetermined time period. The relevant time frame varies with the regimen of drug administration involved. Some drugs must be administered continuously for one or more days. In that instance, a suitable transdermal device would have sufficient drug and antigen processing inhibitor to provide the necessary rate of delivery of up to 24 hours for devices that are replaced periodically or of up to a week for longer-duration devices. Some drugs are only administered once and in that instance, a suitable device would have sufficient drug and antigen processing inhibitor to provide the necessary rates of delivery for a few hours.

The minimum required administration amount and rate of the antigen processing-inhibiting agent in the present invention depends upon a number of factors including the type and amount of sensitizing drug being administered, the period of time over which the drug and the agent are coadministered, the type of action exhibited by the agent (for example, whether it lowers lysosomal pH by interference or accumulation action), and the potency of the agent. Typically, all other variables being equal, the concentrations of accumulative weak base compounds that are required will be higher than the concentrations of ionophores, since their mechanism of action is by accumulation. Thus, the amount of weak base antigen processing-inhibiting agent required to inhibit the processing of a drug as an antigen in the lysosomes is from about 0.2 wt % (weight percent) to about 20 wt % of the drug/agent composition, whereas the amount of ionophere antigen processing-inhibiting agent required is from about 0.01 wt % to about 5 wt %.

The following examples are offered to illustrate the practice of the present inveiton. It is important to note that this invention is not limited to any particular transdermal device or other form of transdermal delivery, as are commonly known in the art. Nor is this inveiton limited to a particular formulation. Therefore, the embodiments described herein are merely illustrative and are not intended to limit the scope of the invention in any manner.

EXAMPLE 1

Reduction of the elicitation phase of sensitization to propranolol, a $\beta$-adrenergic blocker, was demonstrated as follows.

Hydroxyethylcellulose gels buffered to pH 8 and containing 0.5 wt % propranolol and 0, 2, 4, or 8 wt % ammonium chloride were formulated. Twenty microliters of each preparation was applied in duplicate under occlusion for 3 hours on the arm of a human subject known to be sensitized to propranolol. Skin reactions which occurred were evaluated using a Minolta Chromameter. Reaction to propranolol alone reached a maximum at seven days. At this time, a partial inhibition of the elicitation reaction was obtained with all of the ammonium chloride concentrations, and 90% inhibition of the reaction was obtained with 4 wt % of ammonium chloride (see FIG. 4).

EXAMPLE 2

Reduction of the elicitation phase of sensitization to tetracaine was demonstrated as follows.

Hydroxyethylcellulose gels buffered to pH 8 and containing 2.0 wt % tetracaine and 0, 2, 4, or 8 wt % ammonium chloride were formulated. Twenty microliters of each preparation was applied in duplicate under occlusion for 3 hours on the arm of a human subject known to be sensitized to tetracaine. Twenty-one hours later, the reactions were evaluated using a Minolta Chromameter. A partial inhibition of the elicitation reaction was obtained with all of the ammonium chloride concentrations.

EXAMPLE 3

Hydroxyethylcellulose gels buffered to pH 8 and containing 1.0% propranolol and 4 wt % ammonium chloride (gel A) or 1.0% propranolol alone (gel B) are formulated.

Gels are applied to two groups of human subjects. Individuals in group A receive 100 ll of gel A in an aluminum "Finn cup". The application is occluded and left in place for 16 hours. Applications are repeated such that nine applications are spaced out over a three-week period, each application being to a different site on the subject. Subjects in Group B receive gel B which contains propranolol but no ammonium chloride. The gel is applied in the same manner and over the same time period as in group A.

Two weeks after the ninth application is removed, all subjects from both groups receive a 16 hour application of a hydroxyethylcellulose gels buffered to pH 8 and containing 0.1% propranolol (the "challenge" application). Following removal, the site of application is observed and scored for erythema, induration and edema at 2 hr, 24 hr, 48 hr and 72 hr.

In the ten subjects of group A, the site of application shows a slight erythema at the 2 hr reading which progressively decreases in intensity, being only barely perceptible at 24 hr and disappearing by 48 hr. This reaction is typical of minor irrigation and indicates that the subjects did not become sensitized to propranolol.

In eight of the ten subjects in group B, the site of challenge shows a slight erythema at 2 hr, which progressively increases in intensity to reach a peak by 48 hr. In addition, the sites become raised (edematous) and palpable (indurated). In the remaining two subjects of group B, the slight erythema seen at the 2 hr reading progressively decreases, being only slightly perceptible at 24 hr and disappearing by ?hr. Thus, eight of the subjects are sensitized to propranolol, and two show minor irrigation.

The invention reduces the incidence of sensitization to propranolol from 80% to 0%.

While this invention has been described in detail with particular reference to certain preferred embodiments thereof, it will be understood that variations and modifications can be effected without departing from the spirit and scope of the invention as defined in the appended claims.

We claim:

1. A method of reducing or preventing human skin sensitization during transdermal administration to a human of a sensitizing drug, which drug is susceptible to inducing skin sensitization in a human when the drug is transdermally administered, the method comprising coadministering to a selected site on the skin or mucosa of the human:
   (a) a therapeutically effective amount of the sensitizing drug, at a therapeutically effective rate over a predetermined period of time; and
   (b) an antigen processing-inhibiting agent in an amount effective to inhibit the processing of the drug as an antigen, wherein the agent is either an ionophere, in an amount of from about 0.01 wt % to about 5 wt %, or a weak base compound, in an about of from about 0.2 wt % to about 20 wt %.

2. A method according to claim 1 wherein the drug and the agent are coadministered transdermally from a matrix placed in drug and agent transmitting relation with the skin or mucosa.

3. A method according to claim 1 wherein the weak base compound is an amphiphilic amine.

4. A method of reducing or preventing the elicitation of human skin sensitization during transdermal administration to a human of a sensitizing drug to which the human is sensitized, which drug is susceptible to inducing skin sensitization in a human when the drug is transdermally administered, the method comprising coadministering to a selected site on the skin or mucosa of the human:
   (a) a therapeutically effective amount of the sensitizing drug, at a therapeutically effective rate over a predetermined period of time; and
   (b) an antigen processing-inhibiting agent in an amount effective to inhibit the processing of the drug as an antigen, wherein the agent is either an ionophere, in an amount of from about 0.01 wt % to about 5 wt %, or a weak base compound, in an about of from about 0.2 wt % to about 20 wt %.

5. A method according to claim 4 wherein the drug and the agent are coadministered transdermally from a matrix placed in drug and agent transmitting relation with the skin or mucosa.

6. A method according to claim 4 wherein the weak base compound is an amphiphilic amine.

7. A method according to claim 4 wherein the drug is propranolol and the agent is ammonium chloride.

8. A method according to claim 4 wherein the drug is tetracaine and the agent is ammonium chloride.

9. A method of reducing or preventing the induction of human skin sensitization during transdermal administration to a human of a sensitizing drug, which drug is susceptible to inducing skin sensitization in a human when the drug is transdermally administered, the method comprising coadministering to a selected site on the skin or mucosa of the human:
   (a) a therapeutically effective amount of the sensitizing drug, at a therapeutically effective rate over a predetermined period of time; and
   (b) an antigen processing-inhibiting agent in an amount effective to inhibit the processing of the drug as an antigen, wherein the agent is either an ionophere, in an amount of from about 0.01 wt % to about 5 wt %, or a weak base compound, in an about of from about 0.2 wt % to about 20 wt %.

10. A method according to claim 9 wherein the drug and the agent are coadministered transdermally from a matrix placed in drug and agent transmitting relation with the skin or mucosa.

11. A method according to claim 9 wherein the weak base compound is an amphiphilic amine.

12. A transdermal drug delivery device for transdermally administration a sensitizing drug to a human, which drug is susceptible to inducing skin or mucosal sensitization in the human when the drug is transdermally delivered, the device comprising:
   (a) a matrix adapted to be placed in drug and antigen processing-inhibiting agent transmitting relation with a selected site on the skin or mucosa of the human, the matrix containing sufficient amounts of drug and antigen processing-inhibiting agent to continuously and co-extensively administer to the skin or mucosal site:
      (1) a therapeutically effective amount of the sensitizing drug, at a therapeutically effective rate over a predetermined period of time; and
      (2) an antigen processing-inhibiting amount of the antigen processing-inhibiting agent capable of inhibiting processing of the drug as an antigen to reduce or prevent sensitization to the skin or mucosa, wherein the agent is either an ionophore, in an amount of from about 0.01 wt % to about 5 wt %, or a weak base compound, in an amount of from about 0.2 wt % to about 20 wt %.

13. A method according to claim 1 wherein the drug is propranolol and the agent is ammonium chloride.

14. A method according to claim 1 wherein the drug is tetracaine and the agent is ammonium chloride.

15. A method according to claim 12 wherein the drug is propranolol and the agent is ammonium chloride.

16. A method according to claim 12 wherein the drug is tetracaine and the agent is ammonium chloride.

* * * * *

UNITED STATES PATENT AND TRADEMARK OFFICE
CERTIFICATE OF CORRECTION

PATENT NO. : 5,149,539

DATED : September 22, 1992

INVENTOR(S) : Ledger et al.

It is certified that error appears in the above-identified patent and that said Letters Patent is hereby corrected as shown below:

Column 11, line 43, "about" should read --amount--.

Column 12, line 2, "about" should read --amount--; line 28, "about" should read --amount--; line 36, "administration" should read --administering--.

Signed and Sealed this

Fourteenth Day of September, 1993

Attest:

BRUCE LEHMAN

*Attesting Officer*   *Commissioner of Patents and Trademarks*